United States Patent [19]
Bossaert

[11] 4,021,673
[45] May 3, 1977

[54] AXIAL TRANSVERSE TOMOGRAPHY SYSTEM

[75] Inventor: Jean Bossaert, Paris, France

[73] Assignee: Thomson-CSF, Paris, France

[22] Filed: Mar. 15, 1976

[21] Appl. No.: 666,935

[30] Foreign Application Priority Data

Mar. 18, 1975    France .......................... 75.08429

[52] U.S. Cl. .......................... 250/445 T; 250/320
[51] Int. Cl.² .......................... G03B 41/16
[58] Field of Search .......... 250/439 R, 444, 445 R, 250/445 T, 320, 321, 322, 323

[56] References Cited
UNITED STATES PATENTS 2,281,931    5/1942    Frank .......................... 250/445 T
3,746,872    7/1973    Ashe .......................... 250/445 T

*Primary Examiner*—Craig E. Church
*Attorney, Agent, or Firm*—Cushman, Darby & Cushman

[57] ABSTRACT

Axial transverse tomography system analyzing a transverse section of a body by means of a source of X-rays and a detector of X-rays located on opposite sides of the section and in motion about the section. The data received by the detector are employed simultaneously with their formation for an optical reconstitution of the picture from the densities of absorption of the analyzed section. A filter having a predetermined spatial transparency law, associated with the reconstitution optical system, enables a good picture to be obtained.

8 Claims, 6 Drawing Figures

AXIAL TRANSVERSE TOMOGRAPHY SYSTEM

The present invention relates to an axial transverse tomography system which produces pictures of transverse or cross sections of a body to be examined or viewed by absorption of X-rays.

A number of axial transverse tomography systems are now well known.

They comprise for example, an X-ray source and one, or often a plurality of X-ray detectors mounted on a common support. The source and the detectors are so disposed as to be located on opposite sides of the section to be examined or viewed and in its plane. The support is displaced in translation and rotation about this transverse section in such manner that the section is fully swept through by the X-ray beam in a large number of directions.

The detectors reveive at each instant the non-absorbed part of the X-ray beam and transmit to a computer the intensity data of this non-absorbed part of the X-rays. The computer calculates from this data the values of the absorption of each elementary zone (the dimensions of which depend on the resolving power of the system) of the analyzed section and reconstitutes from these calculated values a picture or image of the transverse section.

These systems give very good results but are expensive and space-consuming in that they employ computers for reconstituting the picture of the analyzed transverse sections.

An object of the invention is to provide an axial transverse tomography system comprising an X-ray source and a detector of X-rays which analyze the transverse section of the body to be examined or viewed according to the usual methods of axial trasverse tomography but which permit, simultaneously with this analysis, an optical reconstitution of the picture or image of this section by optical means which are particularly simple, cheap and small compared to computers.

Owing to its optical picture reconstituting system, the system according to the invention produces pictures of good quality which have in particular a suitable contrast.

According to the invention there is provided an axial transverse tomography system for obtaining the pictures of transverse sections of a body comprising: a support displaceable about each section to be examined; a source of X-rays disposed on said support and producing a thin pencil of X-rays which passes through said section; a detector of X-rays disposed on said support and receiving the part of the thin pencil non-absorbed by the passage through said section and converting it into an electric signal whose intensity is proportional to the quantity of non-absorbed X-photons means for amplifying said electric signal; a source of light whose intensity is time modulated by said electric signal; a photographic plate for receiving the light given out by the light source; an optical system disposed between the source and the plate and comprising a filter, said system giving from the source on the plate a two dimensional picture, the light intensity of said picture being spatially constant in a first direction and spatially variable in accordance with a predetermined law in a second direction perpendicular to the first direction; mechanical means acting on at least one element of the assembly: light source-optical system-photographic plate, and displacing it in synchronism with said support so that said first direction of the picture on the photographic plate is constantly homothetic with the direction of the thin pencil on the examined transverse section; said predetermined law being such that the median part of the picture on the plate has a maximum intensity with respect to the parallel parts surrounding it.

A better understanding of the invention will be had from the ensuing description with reference to the accompanying drawings in which.

Figure 4:
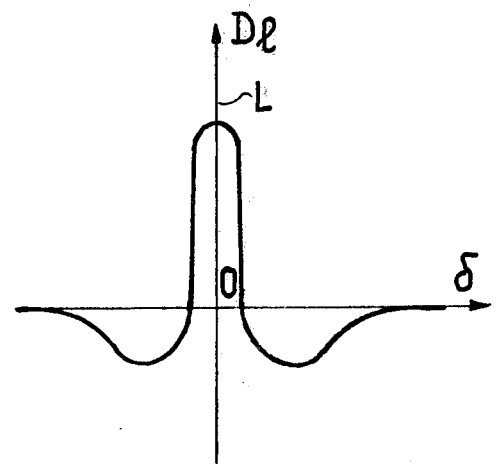
Figure 5:
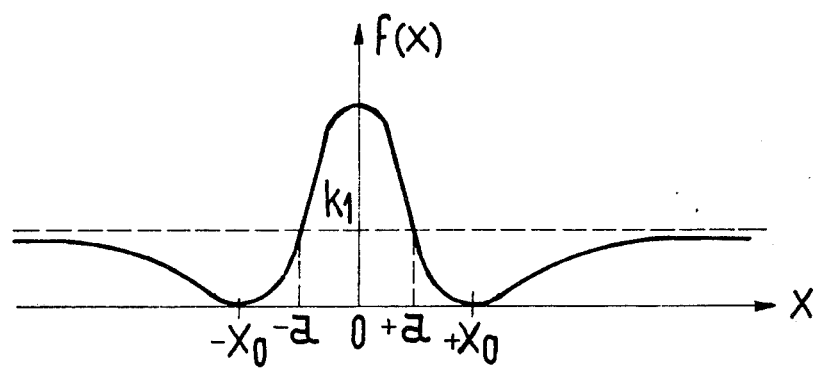
Figure 6:
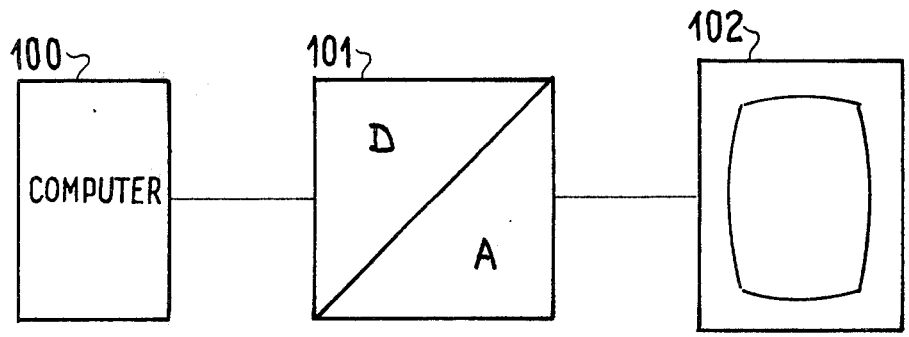

FIG. 4 is a curve showing the ideal distribution curve for obtaining a good contrast; FIG. 5 is a curve showing the configuration of the transparency curve of a filter whereby it is possible to get near to the conditions of FIG. 4; FIG. 6 is a diagrammatic view of a system whereby a filter having a predetermined transparency may be obtained.

Figure 1:
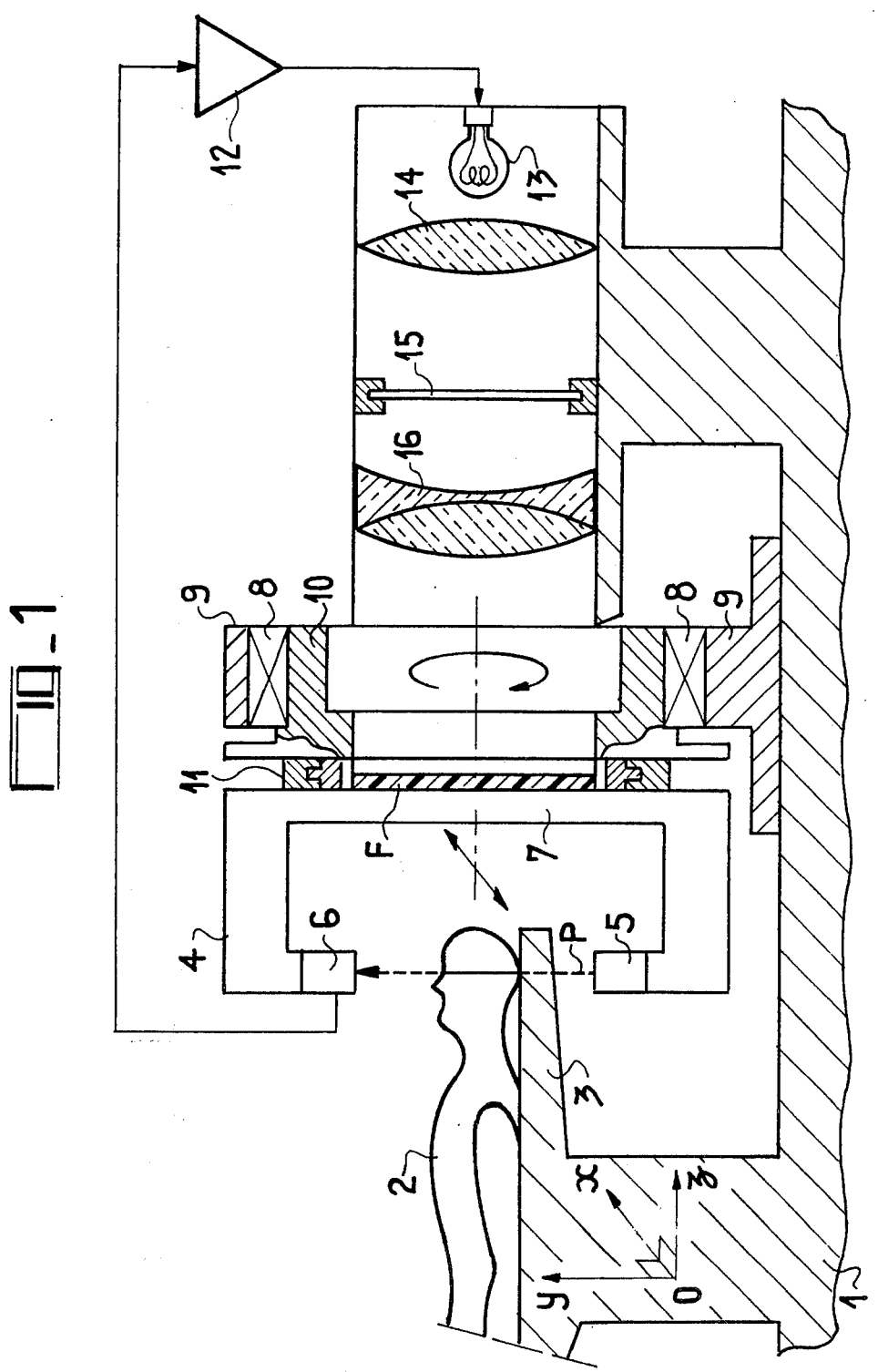
FIG. 1 is a very diagrammatic view of a tomography system according to the invention.

FIG. 1 shows very diagrammatically, and even symbolically for a part, the elements essential to an understanding of a tomography system according to the invention.

A frame 1 here supports all the elements for effecting, on one hand, the analysis of transverse sections or cross-sections S contained in planes parallel the plane (Ox, Oy) of the illustrated tri-right angled reference Ox, Oy, Oz and, on the other, the reconstitution of the picture or image of these sections.

The body 2 to be examined or viewed is placed on a table 3, shown here in the form of a fixed table in order to simplify the illustration. It will be understood that this table is movable relative to the rest of the system, in particular in the direction Ox so as to be capable of examining in succession a plurality of transverse sections with no need to displace the patient 2. The means employed for effecting these displacements are conventional per. se.

The part of the system for analyzing these transverse sections S comprises a support 4, on which there are secured the source 5 of X-rays and the detector 6 of these X-rays. This support is secured by its massive part 7 to mechanical means mounted on the frame 1 whereby the support 4 may be displaced in accordance with the usual methods of axial transverse tomography.

The source 5 of X-rays is disposed at one end of the hollowed-out part of the support and the detector 6 is disposed at the diametrally opposed end of the hollowed-out part of the support. This hollowed-out part surrounds the zone of the body 2 to be examined or viewed.

Figure 2:
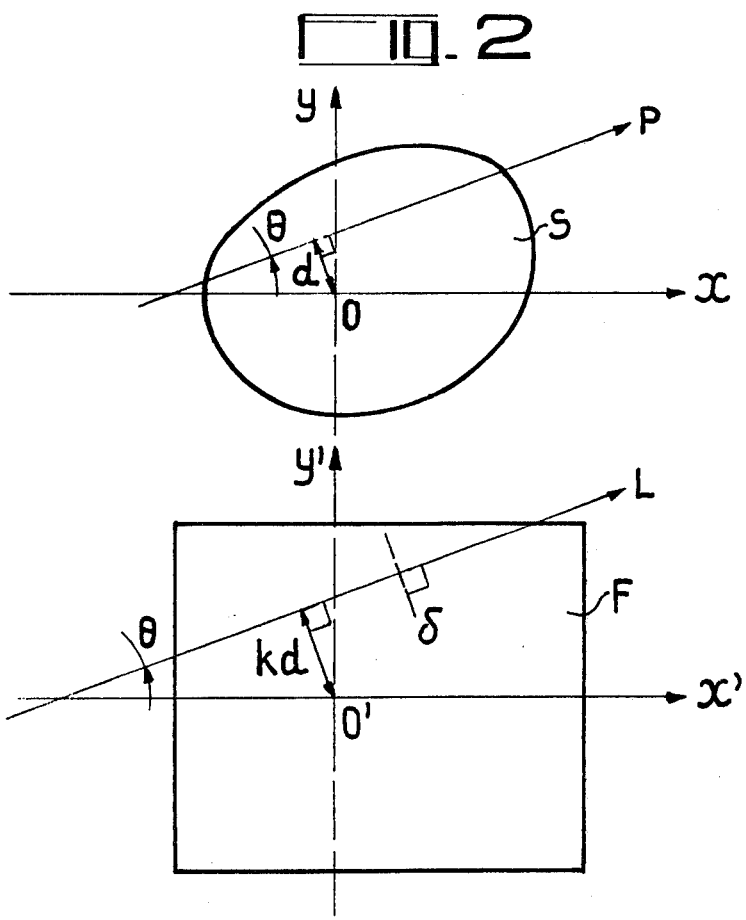
FIG. 2 is a diagrammatic view showing how the pencil P of X-rays and the median part L of the luminous picture are respectively placed on the examine or viewed section S and on the photographic plate F.

The source 5 emits a thin pencil P of X-rays which passes through the section S to be examined before being received by the detector 6. The upper part of FIG. 2 shows the position of this pencil P on the section S; this position is located with respect to a reference Ox, Oy by its distance d from the point O and by the angle $\theta = (\vec{Ox}, \vec{P})$ that the direction of the pencil makes with the axis $\vec{Ox}$.

In order to obtain a suitable analysis of the picture, it is known to displace the support 4 in rotation and in translation about the section S so as to cause the pencil P to sweep through the entire section S, with a large number of different directions for P, or, in other words, with a different angle $\theta$.

This is achieved by conventional means; these means are shown symbolically here by rolling bearings 8 disposed between a hollow shaft 9 mounted on the frame 1 and a second hollow shaft 10 on which the support 4 is mounted. The latter mounting is shown by slideways 11.

The rolling bearings 8 enable the hollow shaft 10 support 4 assembly to rotate about the direction Oz and the slideways 11 enable the support 4 to be moved in translation with respect to the hollow shaft 10. All the desired pencils P ($\theta$, d) can thus be obtained.

The detector 6 detects a quantity of X-rays which is the smaller as the passage through the section S was absorbant and is a function of the position of P in S.

The information or data thus received by the detector 6 is amplified by an amplifier 12 and, instead of being memorized and processed by a computer for a numerical reconstitution of the picture, it is, according to the invention, employed, directly and simultaneously with is formation, for an optical reconstitution of the picture of the analyzed section S.

This optical reconstitution is produced by the following combination of means. A source of light 13 is modulated in intensity by the signal delivered by the amplifier 12. An optical system, here represented by a lens 14, converts the divergent light beam delivered by the source 13 into a beam having parallel rays. This light beam then passes through an optical filter 15 whose law of spatial transparency will be explained and defined hereinafter. An optical system 16 then forms the picture or image of this filter on a photographic plate.

Whereas the source 13, the optical systems 14 and 16 and the filter 15 are mounted on the frame 1, and are consequently stationary, the plate F is, in the presently illustrated embodiment, fixed to the massive part 7 of the support 4 so as to be in a plane parallel to the section S being examined or viewed and to move with the support 4. This plate F is, moreover, so disposed that the luminous picture or image of the filter F is always formed thereon, irrespective of the position of the support 4 in the course of the analysis.

It is also possible to construct the system according to the invention, not by disposing the photographic plate F directly on the support 4, but by securing it on an independent support which reproduces the movements of the support 4 in synchronism therewith. This movement may be reproduced, as desired, to the same scale (as when the plate is fixed directly to the support 4) or to a different scale.

As concerns the filter 15, it may first and in order to have a better understanding of the mechanism for reconstituting the picture of the section S on the photographic plate F, be likened to a simple slit in an opaque wall, this slit being disposed in the middle of the opaque wall in any direction of the plane (Ox, Oy) in which this wall is contained. Thus the source 13 will give a picture or image of the filter on the photographic plate which will be a rectilinear line of light. The light intensity which is constant throughout the length of this line, is time modulated by the signal emitted by the amplifier 12.

The lower part of FIG. 2 shows how this line of light L is disposed on the photographic plate F. As the plate F moves with the direction $\vec{P}$ of the pencil of X-rays, the line L is, at each instant, homothetic in the reference x'O'Y' pertaining in 15 the plate F, with the direction $\vec{P}$ of the pencil in the reference xOy pertaining to the section S. In order to facilitate an understanding of the invention, the two references have been shown parallel; this of course in only true in respect of one position of the support, since the plate F and its reference turn therewith; this case may be chosen by convention as being that in which the pencil P is parallel to the direction of the line L. To simlify the language, it will be said hereinafter that the line L is homothetic, on the plate F, with the pencil P, on the section S. This line L makes an angle $\theta$ the axis $\vec{O'x'}$ and is spaced from O' a distance Kd, in which K is a coefficient of similarity.

In the case illustrated here, in which the movement of the plate F integral with the support 4 is that of this support and in which the picture that will be reconstituted on the plate F is to scale 1, there is obtained K = 1.

It other cases, it is possible to obtain a reconstituted picture or image with a scale different from 1. In this case there is obtained K $\neq$ 1 (as illustrated in the upper part of FIG. 2). It is sufficient, for example, to employ a reducing or enlarging system of the pantograph type between the support 4 moving the pencil P and the photographic plate F.

The photographic plate F, thus swept through by the line L which is homothetic with P and has an intensity which is a function of the part of P which is not absorbed by the corresponding passage through the section S, carries a picture of image which is the reconstitution of the density of absorption of the X-rays in the viewed or examined section S.

Figure 3:
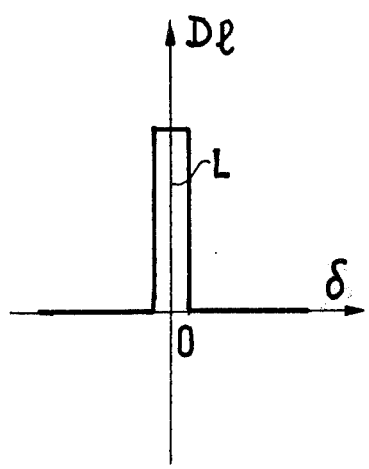
FIG. 3 is a curve showing the possibility of distribution of light $D_1$ producing a picture of medium quality.

If the filter F is, as mentioned hereinbefore, a simple slit in an opaque plate, the light distribution on the photograhic plate F in a direction $\delta$ perpendicular to the line L of the slit is given by the curve $D_1 = f(\delta)$ of FIG. 3, in which the axis $D_1$ represents the direction of the line L.

Such a light distribution does not permit obtaining a restored picture which suitably differentiates the differences of absorption in the examined or viewed transverse section. It only permits the obtainment of a "ghost" picture of the same form as the examined section but whose different levels of absorption are poorly defined.

A very simplified explanation will enable the reason for this poor definition to be perceived. The line L of constant intensity throughout its length symbolises the total absorption of the pencil P in its corresponding passage through the section S, without, of course, differentiating the differences of absorption along the path of this pencil. These differences are only obtained upon the reconstitution of the picture, by the combination, at each point of the plate, of the different lines L (of different $\theta$ and different light intensities). If the distribution of light $D_1$ along $\delta$ is such that of FIG. 3, "reinforcements" of absorption will be possible, but not "weakenings". Now, both are necessary to the obtainment from an initial level which may be according to the points of the line L, too strong or too weak with respect to the real level of absorption of the corresponding zone of the analyzed section S.

If, on the other hand, the light distribution curve along this same axis $\delta$ were as that shown in FIG. 4, the restored picture would have a good representation of the different levels, since there would be a possibility of both "reinforcing" ($D_1<0$) and "weakening" ($D_1<0$).

As it is of course impossible to obtain $D_1<0$, the invention teaches the use at 15 of an optical filter whereby it is possible to obtain the equivalent of the curve shown in FIG. 4. Such a filter has a uniform transparency along a first direction of its plane (parallel to the plan (Ox, Oy) of the reference) and its transparency curve varies along a second direction, perpendicular to the first directions according to a law as illustrated by the curve shown in FIG. 5.

Here again, as in the case of the slit, said first direction may be oriented in any way in the plane of the filter; the line L on the photographic plate will be parallel to said first direction and will have a light intensity distribution conforming with the curve shown in FIG. 4, except that there will be a continuous luminous background throughout the picture.

In order that the reconstitution be correct, the curve shown in FIG. 5 must satisfy two conditions.

The two parts of the curve situated on each side of the median part (between $X==X_o$ and $X=+X_o$) must tend toward a constant attenuation equal to $k_1$, by lower value, and in a manner inversely proportional to the square of the distance to the centre. The function $f(X)$ will therefore be, for these curve parts, of the form:

$$f(X) \sim k_1 - \frac{k_2}{X^2}$$

in which $k_1$ determines the continuous background of the picture, and $k_2$ is the contrast constant of the picture, the contrast obtained being proportional thereto.

The second condition is that the whole of the function: median part and lateral parts of the curve, allow the value $k_1$ to be the mean value, that is to say that the area of the function above the asymptote $k_1$ is equal to the area below this asymptote.

It must also be noted that the median part of the curve: $-X_0<X<+X_o$ whose maximum value corresponds, for example, to zero opacity of the filter, is very narrow with respect to the total dimension of the filter along the axis Ox.

The minima have been taken here as nil, that is, they correspond to a complete opacity. This, although not necessay, is preferable in order to avoid an excessively large continuous background $k_1$.

FIG. 6 gives very diagrammatically an embodiment of means for obtaining a filter having a predetermined transparency curve, such as that shown in FIG. 5. The law of the chosen function is fed into a computer 100 whose output is connected to a digital analog converter 101. The output of the latter is connected to an oscilloscope tube 102 whose beam sweeps the target in accordance with a television type of line sweep. The intensity of this beam is modulated in the course of the sweep in accordance with the transparence to be obtained. The picture or image obtained on this tube is then photographed; the photographic picture constitutes the required filter.

It may also be noted that the foregoing description, the homothetic displcement, of the line L on the plate F and the pencil P on the section S were achieved by displacing the plate F.

It is also possible, according to the invention, to maintain the plate F stationary and to displace, in synchronism with the support 4, the filter and its associated optical system, namely the source and the lenses. In this case, the pencil P and the line L are displaced together on stationary surfaces (section S and plate F).

It will be understood that in all cases the optical system-filter-photographic plate must be located in a dark room.

What is claimed is:

1. An axial transverse tomography system for obtaining pictures of transverse sections of a body, comprising:

a support displaceable about each section to be examined;

a source of X-rays on this support, emitting a thin pencil passing through this section;

a detector of X-rays on said support, receiveing the part of the thin pencil non-absorbed by the passage through said section, and converting it into an electric signal whose intensity is proportional to the quantity of non-absorbed X-photons;

means for amplifying said electric signal;

a source of light whose intensity is time modulated by said electric signal;

a photographic plate for receiving the light given out by the source of light;

an optical system placed between the source and the plate and comprising a filter, said system producing from the source in the plate a two dimensional picture, the light intensity of said picture being spatially constant along a first direction and spatially variable, in accordance with a predetermined law, along a second direction perpendicular to the first direction;

mechanical means acting on at least one element of the assembly: light source-optical system-photographic plate, and displacing it in synchronism with said support so that said first direction of the image on the photographic plate is constantly homothetic with the direction of the thin pencil on the examined transverse section;

said predetermined law being such that the median part of the picture on the plate has a maximum intensity with respect to the parallel parts surrounding it.

2. A tomography system as claimed in claim 1, wherein the photographic plate is displaced in synchronism with said support so that said first direction of the picture on the photographic plate is constantly homothetic with the direction of the thin pencil on said transverse section, the source of light and the optical system being stationaring.

3. A system as claimed in claim 2, wherein the photographic plate is secured to said support in a plane parallel to the plane of the examined transverse sections.

4. A system as claimed in claim 2, wherein the photographic plate is displaced by mechanical means distinct from said support.

5. A system as claimed in claim 4, wherein means for connecting the amplitude of the movements of said support are disposed between said support and the means for displacing the photographic plate.

6. A system as claimed in claim 1, wherein said filter has along said second direction a transparency curve symmetrical with respect to the axes of symmetry of said filter parallel to said first direction; said curve having in its median part ($X =$ ) a maximum of transparency, decreasing on each side of said maximum toward two minima ($X = \pm X_o$), and comprising around said median part, two parts tending toward a constant transparency $k_1$, by lower value and in a manner inversely proportional to the centre (X = 0) ; said curve being such that its function allows said value of constant transparency $k_1$ to be said mean value.

7. A system as claimed in claim 6, wherein said transparency minima (X = $\pm X_o$) correspond to zero transparency.

8. A system claimed in claim 6, wherein the width of said median part of the transparency curve of the filter is chosen as a function of the required resolving power.

* * * * *